(12) United States Patent
Oba et al.

(10) Patent No.: US 11,963,760 B2
(45) Date of Patent: Apr. 23, 2024

(54) MEASURING DEVICE, BLOOD-SUGAR LEVEL MEASURING DEVICE, AND MEASURING METHOD

(71) Applicants: Yoshihiro Oba, Miyagi (JP); Ryosuke Kasahara, Kanagawa (JP); Toshihide Sasaki, Kanagawa (JP); Nobuto Hosono, Hyogo (JP)

(72) Inventors: Yoshihiro Oba, Miyagi (JP); Ryosuke Kasahara, Kanagawa (JP); Toshihide Sasaki, Kanagawa (JP); Nobuto Hosono, Hyogo (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 18/120,433

(22) Filed: Mar. 13, 2023

(65) Prior Publication Data
US 2023/0293052 A1    Sep. 21, 2023

(30) Foreign Application Priority Data

Mar. 18, 2022    (JP) .................................. 2022-044641

(51) Int. Cl.
*A61B 5/145*    (2006.01)
*A61B 5/00*    (2006.01)

(52) U.S. Cl.
CPC ............ *A61B 5/145* (2013.01); *A61B 5/0059* (2013.01)

(58) Field of Classification Search
CPC ....... A61B 5/145; A61B 5/0059; A61B 5/682; A61B 5/6826; A61B 5/0086; A61B 5/14532
See application file for complete search history.

(56) References Cited

U.S. PATENT DOCUMENTS

| | | | |
|---|---|---|---|
| 2020/0170553 A1 | 6/2020 | Kasahara et al. | |
| 2021/0259586 A1 | 8/2021 | Oba et al. | |

(Continued)

FOREIGN PATENT DOCUMENTS

| | | |
|---|---|---|
| JP | 6-281568 | 10/1994 |
| JP | 2003-042948 | 2/2003 |
| JP | 2011-220962 | 11/2011 |

(Continued)

*Primary Examiner* — Tony Ko
(74) *Attorney, Agent, or Firm* — XSENSUS LLP

(57) ABSTRACT

A measuring device includes a total internal reflection prism having a total reflection plane that an object to be measured contacts, a light source to emit light to make the light having a wavelength equal to or greater than 7 micrometers (μm) and equal to or less than 12 μm incident on the total reflection plane, and a sensor to detect light intensity of the light reflected by the total reflection plane. In the measuring device, an equation $$\arcsin\left(\frac{n2}{n1}\right) < \theta c < \arcsin\left(\frac{n2}{n1}\right) + 5.0 \ [DEG]$$

is satisfied, where n1 denotes a refractive index of a base material of the total internal reflection prism for the light having a wavelength of 10 μm, n2 denotes a refractive index of the object to be measured for the light having the wavelength of 10 μm and n2 takes a value 1.32 or 1.44, and θc denotes an incident angle of a center of light flux emitted from the light source.

20 Claims, 11 Drawing Sheets

(56) References Cited

U.S. PATENT DOCUMENTS

2022/0369963 A1\* 11/2022 Oba ................ A61B 5/14532
2022/0386875 A1 12/2022 Oba et al.

FOREIGN PATENT DOCUMENTS

| JP | 2019-037752 | 3/2019 |
| JP | 2021-074526 | 5/2021 |
| JP | 2023-015889 | 2/2023 |

\* cited by examiner

MEASURING DEVICE, BLOOD-SUGAR LEVEL MEASURING DEVICE, AND MEASURING METHOD

CROSS-REFERENCE TO RELATED APPLICATION

This patent application is based on and claims priority pursuant to 35 U.S.C. § 119(a) to Japanese Patent Application No. 2022-044641, filed on Mar. 18, 2022, in the Japan Patent Office, the entire disclosure of which is hereby incorporated by reference herein.

BACKGROUND

Technical Field

Embodiments of the present disclosure relate to a measuring device, a blood-sugar level measuring device, and a measuring method.

Background Art

Measuring devices have been proposed that perform measurement using the light having the wavelength in the middle range of infrared light. Typically, such a wavelength in the middle range of infrared light includes a wavelength of about 10 micrometers (μm). Such measuring devices are used to measure, for example, the blood sugar level of a live subject. Currently, the number of patients who suffer from diabetes is increasing all over the world. For this reason, there are increasing demands for, for example, noninvasive measuring devices that measure the blood sugar level but do not require blood drawing.

Typically, such measuring devices that use the mid-infrared light use the wave number of the peak of glucose absorbance such as 1035 centimeters $(cm)^{-1}$, 1080 $cm^{-1}$, and 1110 $cm^{-1}$ in order to accurately measure the glucose concentrations in a specific wavelength range such as the middle range of infrared light using the attenuated total reflection (ATR).

SUMMARY

Embodiments of the present disclosure described herein provide two measuring devices. One measuring device includes a total internal reflection prism having a total reflection plane that an object to be measured contacts, a light source to emit light to make the light having a wavelength equal to or greater than 7 micrometers (μm) and equal to or less than 12 μm incident on the total reflection plane, and a sensor to detect light intensity of the light reflected by the total reflection plane. In the one measuring device, an equation $$\arcsin\left(\frac{n2}{n1}\right) < \theta c < \arcsin\left(\frac{n2}{n1}\right) + 5.0 \ [DEG]$$

is satisfied, where n1 denotes a refractive index of a base material of the total internal reflection prism for the light having a wavelength of 10 μm, n2 denotes a refractive index of the object to be measured for the light having the wavelength of 10 μm and n2 takes a value 1.32 or 1.44, and θc denotes an incident angle of a center of light flux emitted from the light source. Another measuring device includes a total internal reflection prism having a total reflection plane that an object to be measured contacts, the total internal reflection prism having a base material with a refractive index n1, a light source to emit light to make the light having a wavelength equal to or greater than 7 micrometers (μm) and equal to or less than 12 μm incident on the total reflection plane, and a sensor to detect light intensity of the light reflected by the total reflection plane. In the other measuring device, the refractive index n1 of the base material of the total internal reflection prism for the light having a wavelength of 10 μm is greater than 1.32 and equal to or smaller than 1.91.

BRIEF DESCRIPTION OF THE DRAWINGS

A more complete appreciation of embodiments and the many attendant advantages thereof will be readily obtained as the same becomes better understood by reference to the following detailed description when considered in connection with the accompanying drawings.

Figure 1:
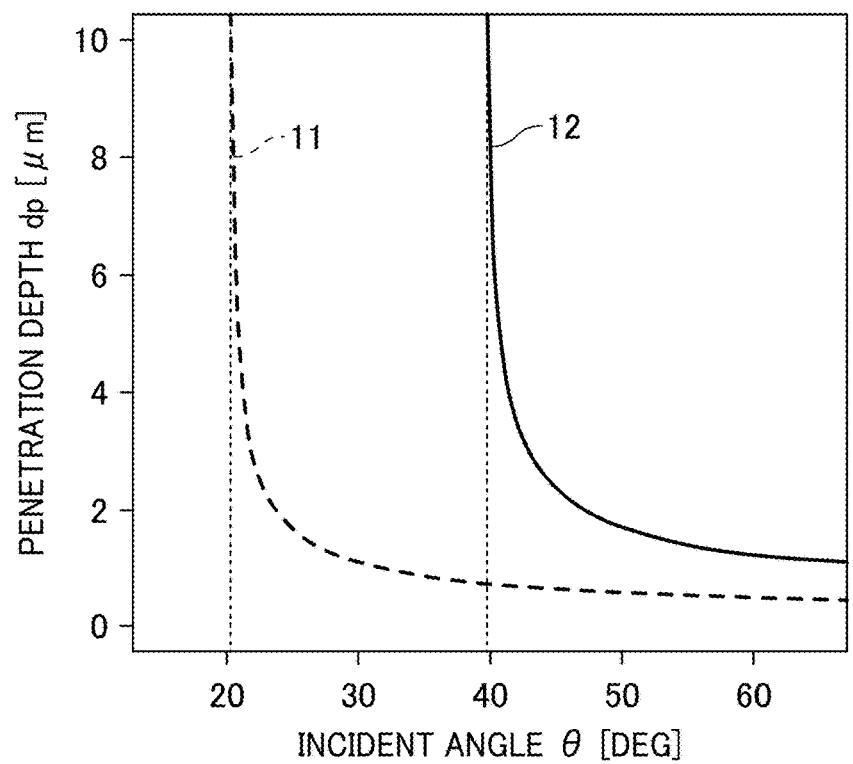
FIG. 1 is the first diagram illustrating the relation between the penetration depth and the incident angle, according to the related art.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

Embodiments of the present disclosure are described below with reference to the accompanying drawings. In the drawings, like reference signs denote like elements, and overlapping description may be omitted where appropriate. A measuring device according to embodiments of the present disclosure is described below to implement the technical ideas, and no limitation is indicated to the embodiments of the present disclosure given below. For example, the size, material, and shape of components and the relative positions of the arranged components are given by way of example in the following description, and the scope of the present disclosure is not limited thereto unless particularly specified. For example, the size of these elements and the relative positions of these elements may be exaggerated for purposes of illustration in the drawings.

A measuring device that adopts the attenuated total reflection (ATR) to measure the blood sugar level as live-subject information based on the absorbance, according to embodiments of the present disclosure, is described below.

Approximately, the middle range of infrared light indicates a wavelength range between 2 micrometers (μm) and 14 μm.

In the attenuated total reflection, the evanescent wave that is emitted from the total reflection plane is used to obtain the spectrum characteristics of the absorbance of the object to be measured when total internal reflection occurs in a total internal reflection prism arranged in contact with an object to be measured.

Absorbance is a dimensionless quantity that indicates how much light intensity decreases when the light passes through an object. In the present embodiment, the attenuated total reflection is adopted. For example, an evanescent wave is emitted from the total reflection plane, and the attenuation of the evanescent wave by a live subject is measured as the degree of absorbance using the ATR.

The blood sugar level indicates the density or concentration of glucose included in the blood.

The relation between the wavelength λ (μm) and the wave number k (cm$^{-1}$) is indicated by the equation given below.

$$k = 10000/\lambda$$

The necessity to reveal the refractive index of the object to be measured in the middle range of infrared light, a method of measuring the refractive index of the object to be measured in the middle range of infrared light, and a result of measuring the refractive index of the object to be measured in the middle range of infrared light in the measurement using the ATR are described below. Typically, the object to be measured S in the present embodiment is a live subject such as a lip and finger.

For example, the penetration depth dp is defined as a sixth formula given below. The penetration depth dp indicates how deep the evanescent wave emitted from the total reflection plane of the total internal reflection prism penetrates into the object to be measured that contacts the total reflection plane. The penetration depth dp can be as deep as when the light intensity of the evanescent wave that has penetrated into the object to be measured is reduced to 1/e.

$$dp = \frac{\lambda}{2 \cdot \pi \cdot n1 \cdot \sqrt{\sin^2\theta - \left(\frac{n2}{n1}\right)^2}} \quad \text{Sixth Formula}$$

In the sixth formula, θ denotes the incident angle that the light forms with the total reflection plane. λ denotes the wavelength included in the light. π denotes the Ludolphian number that is also referred to as a circular constant. n1 denotes a refractive index of the base material of a total internal reflection (TIR) prism.

n2 denotes a refractive index of an object to be measured.

The refractive index n1 and the refractive index n2 as will be described later indicate the refractive indexes with respect to the light including wavelengths of 10 μm.

According to the sixth formula as given above, each one of the relation between the penetration depth and the incident angle θ when the base material of the total internal reflection prism includes germanium (Ge) and the relation between the penetration depth and the incident angle θ when the base material of the total internal reflection prism includes zinc sulfide (ZnS) is as illustrated in FIG. 1.

FIG. 1 is a diagram illustrating the relation between the penetration depth and the incident angle θ when the refractive index n2 is assumed to be 1.400 which is an estimated value known in the art, according to an embodiment of the present disclosure.

In FIG. 1, the graph 11 that is indicated by dashed lines illustrates a case in which the germanium (Ge) whose refractive index n1 is 4.00 is used, and the graph 12 that is indicated by a solid line illustrates a case in which the zinc sulfide (ZnS) whose refractive index n1 is 2.20 is used.

On the surface of a live subject such as a lip or a finger, there is a stratum corneum which is considered to contain no glucose. The thickness of the stratum corneum varies from site to site. Approximately, the thickness of a lip is equal to or greater than 2 micrometers (μm) and equal to or smaller than 4 μm. Approximately, the thickness of a finger is equal to or greater than 10 μm and equal to or smaller than 20 μm. The penetration depth dp is preferably deeper than the depth corresponding to the thickness of the stratum corneum such that the absorbance can be measured in a region deeper than the stratum corneum in the live subject. However, in the related art, the refractive index n2 of the object to be measured with respect to the light including wavelengths of 10 μm is not sufficiently examined and made clear, and an optimum incident angle θc was unknown. Accordingly, it was difficult to perform measurement using the ATR at the penetration depth dp deeper than the depth corresponding to the thickness of the stratum corneum.

Figure 2:
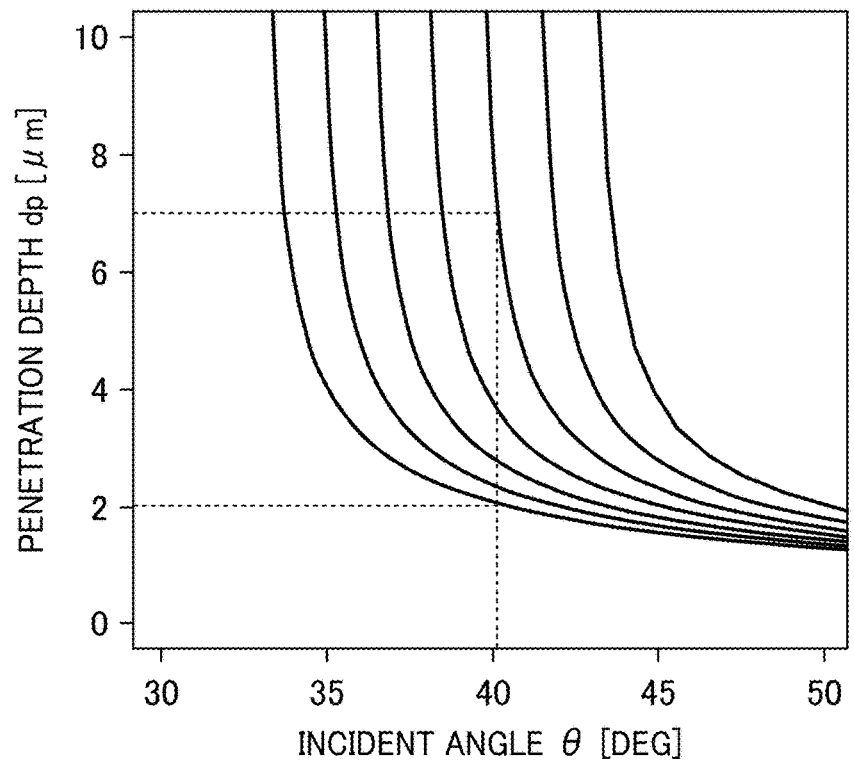
FIG. 2 is the second diagram illustrating the relation between the penetration depth and the incident angle, according to the related art.

FIG. 2 is a diagram illustrating the relation between the penetration depth and the incident angle θ, according to the second example of the present disclosure.

More specifically, FIG. 2 illustrates the penetration depth dp when a refractive index n1 of the base material of a total internal reflection prism is 2.20 and the refractive index of an object to be measured is changed. The multiple graphs in FIG. 2 illustrate the relations between the penetration depth dp and the incident angle θ in the order from the smallest value to the largest value of the incident angle θ when the refractive index n2 is 1.20, 1.25, 1.30, 1.35, 1.40, 1.45, and 1.50. For example, when the incident angle θ is 40.0 degrees, the penetration depth dp changes from about 2 μm to about 7 μm depending on the refractive index n2 of an object to be measured.

As the incident angle θ gets close to a critical angle θ0 as defined by an equation given below, the penetration depth dp increases.

$$\theta 0 = \arcsin(n2/n1)$$

However, if the incident angle θ decreases and becomes narrower than the critical angle θ0, the light that is incident on the total reflection plane is not totally reflected, but the light passes through the total internal reflection prism and then is absorbed into the object to be measured. In such cases, measurement using the ATR cannot successfully be performed. For this reason, when an object to be measured whose refractive index n2 is not clear is to be measured using the ATR, an incident angle θ that maximizes the penetration depth dp is to be clarified in advance.

In order to increase the degree of reliability in the above measurement, it is desired that the refractive index n1 of the base material of a total internal reflection prism be closed to the refractive index n2 of an object to be measured. In the related art, the precise value of the refractive index of a live subject with respect to the light in the mid-infrared range is not revealed. However, it is estimated that the refractive index of a live subject with respect to the light in the mid-infrared range ranges from 1.20 to 1.50. The germanium (Ge) whose refractive index n1 is 4.0 and the zinc sulfide (ZnS) whose refractive index n1 is 2.20 has a relatively large difference in refractive index with the refractive index n2 of the object to be measured, which ranges from 1.20 to 1.50 as described above.

Using the critical angle method, it can be revealed that the refractive index of a lip with respect to the light including wavelengths of 10 μm is 1.32 and the refractive index of a finger with respect to the light including wavelengths of 10 μm is 1.44.

Figure 3:
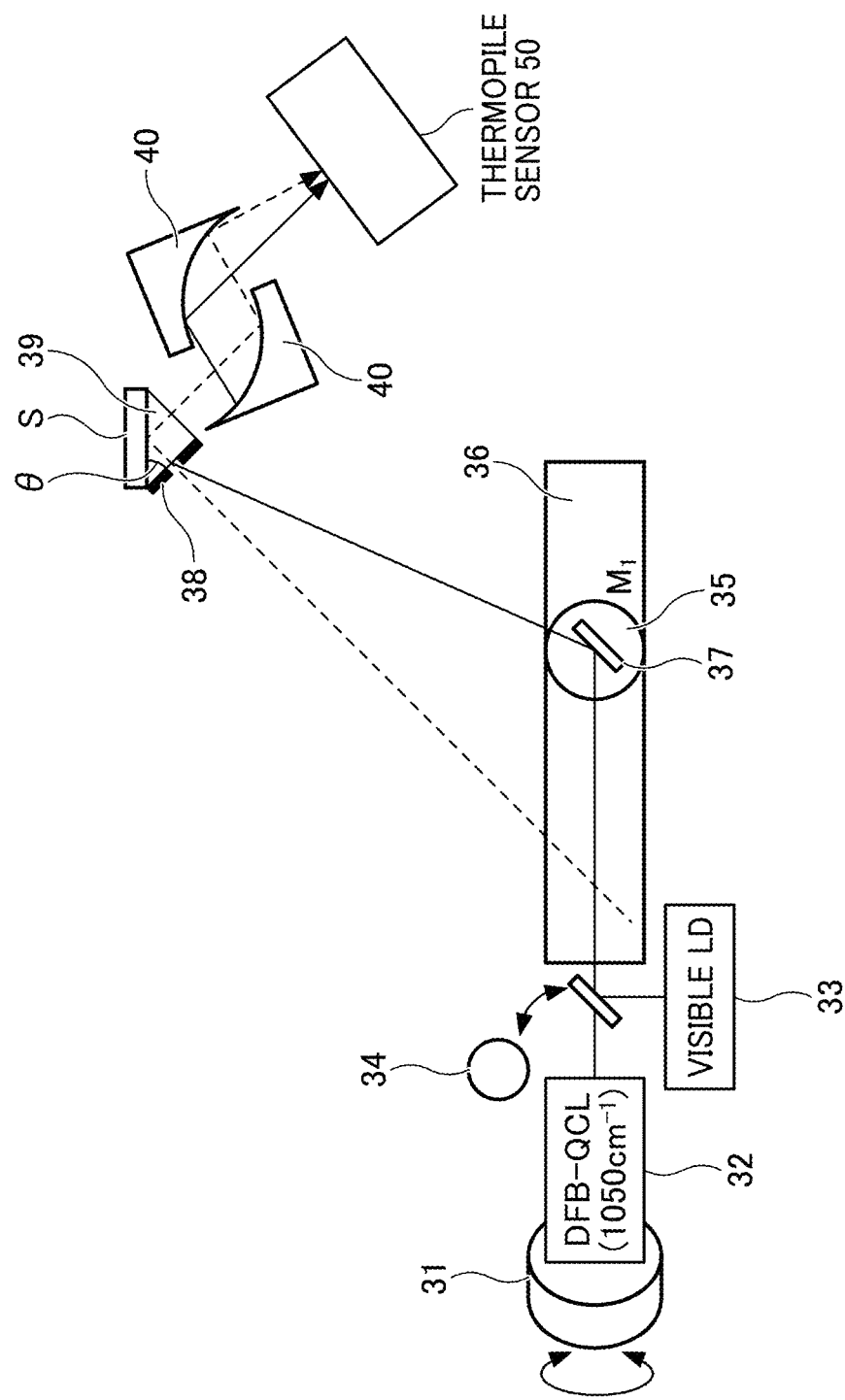
FIG. 3 is a diagram illustrating how a refractive index is measured using a critical angle method, according to the related art.

FIG. 3 is a diagram illustrating how a refractive index is measured using a critical angle method, according to the related art.

The configuration or structure illustrated in FIG. 3 in which a refractive index is measured using a critical angle method includes, for example, a first rotatable stage 31, a distributed feedback quantum cascade laser (QFB-QCL) 32, a laser diode (LD) 33, an optical-path switching mirror 34, a second rotatable stage 35, a parallel stage 36, a mirror 37, an aperture 38, a prism 39, a parabolic mirror pair 40, and a thermopile sensor 50. In FIG. 3, S denotes an object to be measured.

The distributed feedback quantum cascade laser 32 according to the present embodiment is a light source to emit the light of wave number 1050 cm$^{-1}$. The light emitted from the distributed feedback quantum cascade laser 32 is reflected by the mirror 37 toward the aperture 38 and enters the prism 39 through the aperture 38. The light incident on the prism 39 is reflected by the surface that the object to be measured S contacts, and then exits from the prism 39. Subsequently, the light is concentrated onto the thermopile sensor 50 by the parabolic mirror pair 40. The thermopile sensor 50 according to the present embodiment outputs the information about the amount of the concentrated light.

When the refractive index n1 of the prism 39 is higher than the refractive index n2 of the object S to be measured, the light incident on the prism 39 is totally reflected by the prism 39 until the incident angle θ reaches the critical angle θ0. In view of these circumstances, the critical angle θ0 is calculated using the prism 39 whose refractive index n1 is known when the object to be measured S contacts the prism 39. By so doing, unknown refractive index n2 of the object to be measured S can be measured. In the related art, the refractive index n2 of the object to be measured S in the middle range of infrared light has never been revealed in any report. In the present disclosure, the refractive index n2 of the object to be measured S in the middle range of infrared light is revealed for the first time in the related art.

In the present example, the base material of the total internal reflection (TIR) prism where the difference in the refractive index with the object to be measured S is small is diligently examined. Firstly, a plurality of total internal reflection prisms whose base materials have different refractive indexes n1 are used, and comparison is made in relation to the relation between the penetration depth dp and the incident angle θ formed with the object to be measured S whose refractive index is n2.

The first table indicates the relation between the penetration depth dp and the incident angle θ in various kinds of combinations of the refractive index n1 of the total internal reflection prism and the refractive index n2 of the object to be measured S, according to the present example.

| | First Table | | | | | |
|---|---|---|---|---|---|---|
| | EX. 1 | EX. 2 | EX. 3 | EX. 4 | EX. 5 | EX. 6 |
| n1 | 1.51 | 1.91 | 2.2 | 1.53 | 1.57 | 2.2 |
| n2 | 1.32 | 1.32 | 1.32 | 1.44 | 1.44 | 1.44 |
| INCIDENT ANGLE θ0 [DEG] | 60.9 | 43.7 | 36.9 | 70.3 | 66.5 | 40.9 |
| dp [μm] WHEN INCIDENT ANGLE IS "θ0 + 0.8 [DEG]" | 9.7 | 7.1 | 6.2 | 11.1 | 10.1 | 6.1 |
| dp [μm] WHEN INCIDENT ANGLE IS "θ0 + 1.0 [DEG]" | 8.7 | 6.3 | 5.6 | 10.0 | 9.1 | 5.5 |

-continued

First Table

|  | EX. 1 | EX. 2 | EX. 3 | EX. 4 | EX. 5 | EX. 6 |
|---|---|---|---|---|---|---|
| dp [μm] WHEN INCIDENT ANGLE IS "θ0 + 5.0 [DEG]" | 4.0 | 2.8 | 2.5 | 4.7 | 4.2 | 2.5 |
| dp [μm] WHEN INCIDENT ANGLE IS "θ0 + 10.0 [DEG]" | 2.9 | 2.0 | 1.7 | 3.6 | 3.1 | 1.7 |

When the measurement is performed using the configuration or structure described above with reference to FIG. 3, the refractive index of the lips of a live subject is about 1.28 to 1.36, and the refractive index of a finger of a live subject is about 1.442 to 1.446. In the calculation depicted in the first table, the wavelength λ is 10 micrometers (μm), and the refractive index n2 of the object to be measured is 1.32 or 1.44.

According to the first table given above, it is understood that the penetration depth dp increases around the critical angle θ0 and the ranges of angle for the degree of penetration depth dp is widened around the critical angle θ0 as the refractive index n1 of the prism is closer to the refractive index n2 of the object to be measured. For example, in the case of the Example 2 (EX. 2) where the refractive index n1 and the refractive index n2 were 1.91 and 1.32, respectively, the penetration depth dp became equal to or smaller than 2 μm as in "dp≥2 μm" when the incident angle θ was equal to or wider than the critical angle θ0 that is 43.7 degrees and equal to or narrower than "θ0+10.0" degrees. Moreover, it is understood that, when the refractive index n2 is 1.32, a greater degree of penetration depth dp can be achieved compared with cases in which total internal reflection (TIR) prisms known in the art that include zinc sulfide (ZnS) as part of the base material are used. It is also understood that a deeper degree of penetration depth dp than an unmeasurable depth of about 2 μm can be achieved.

In the case of Example 1 (EX. 1) where the refractive index n1 and the refractive index n2 were 1.51 and 1.32, respectively, the penetration depth dp became equal to or smaller than 2 μm as in "dp≥2 μm" when the incident angle θ was equal to or wider than the critical angle θ0 that is 60.9 degrees and equal to or narrower than "θ0+10.0" degrees. Moreover, the penetration depth dp became equal to or greater than 4 μm as in "dp≥4 μm" when the incident angle θ was equal to or wider than the critical angle θ0 and equal to or narrower than "θ0+5.0" degrees. For example, it is understood that, when the refractive index n2 is 1.32, a deeper degree of penetration depth dp than an unmeasurable depth of about 2 μm can be achieved.

In the case of Example 5 (EX. 5) where the refractive index n1 and the refractive index n2 were 1.57 and 1.44, respectively, the penetration depth dp became equal to or greater than 10 μm as in "dp≥10 μm" when the incident angle θ was equal to or wider than the critical angle θ0 that is 67.0 degrees and equal to or narrower than "θ0+0.8" degrees. For example, it is understood that, when the refractive index n2 is 1.44, a deeper degree of penetration depth dp than an unmeasurable depth of about 10 μm can be achieved.

In the case of Example 4 (EX. 4) where the refractive index n1 and the refractive index n2 were 1.53 and 1.44, respectively, the penetration depth dp became equal to or greater than 10 μm as in "dp≥10 μm" when the incident angle θ was equal to or wider than the critical angle θ0 that is 70.8 degrees and equal to or narrower than "θ0+1.0" degrees. For example, it is understood that, when the refractive index n2 is 1.44, a deeper degree of penetration depth dp than an unmeasurable depth of about 10 μm can be achieved.

Based on the results indicated in the first table, it is determined in view of the safety to the live subject and the transmittance in the mid-infrared range that sodium chloride (NaCl) is to be used as the base material of the total internal reflection (TIR) prism. The refractive index of sodium chloride (NaCl) in the middle range of infrared light is approximately 1.49. When the refractive index n1 and the refractive index n2 take values that are very close to each other, the critical angle θ0 gets close to 90 degrees, and penetration cannot be achieved unless the angle is very close to 90 degrees. As there are some individual variations in the refractive index n2, the refractive index n1 tends to be smaller than the refractive index n2. In view of the above circumstances, it is desired that the refractive index n1 of the prism be at least slightly different from the refractive index n2 of the object to be measured. Also from this viewpoint, it is desired that sodium chloride (NaCl) that has the refractive index of 1.49 be used as the base material of the total internal reflection prism with which a live subject is measured as an object to be measured.

As described above, it is revealed in the present example that the refractive index n2 of the object to be measured S is 1.32 or 1.44. As the incident angle θ to the total reflection plane is closer to the critical angle θ0, the degree of penetration depth dp with reference to the object to be measured S increases. In view of the above circumstances, it is desired that the incident angle θc angle which the center of the light flux from the light source forms with the total reflection plane satisfy the first formula given below.

$$\arcsin\left(\frac{n2}{n1}\right) < \theta c < \arcsin\left(\frac{n2}{n1}\right) + 5.0 \ [DEG] \quad \text{First Formula}$$

In the present embodiment, when it is assumed that the refractive index n2 of the object to be measured S with respect to the light including wavelengths of 10 μm is 1.32 and the light having the wavelength of 10 μm is incident on the total reflection plane at the incident angle θ, it is desired that the refractive index n1 satisfy the second formula and third formula given below.

$$\theta = \arcsin\left(\frac{n2}{n1}\right) + 10.00 \ [DEG] \quad \text{Second Formula}$$

$$\frac{\lambda}{2 \cdot \pi \cdot n1 \cdot \sqrt{\sin^2\theta - \left(\frac{n2}{n1}\right)^2}} \geq 2 \ [\mu m] \quad \text{Third Formula}$$

In the present embodiment, when it is assumed that the refractive index n2 of the object to be measured S with respect to the light including wavelengths of 10 µm is 1.32 and the light having the wavelength of 10 µm is incident on the total reflection plane at the incident angle θ, it is desired that the refractive index n1 satisfy the second formula and third formula given below.

$$\theta = \arcsin\left(\frac{n2}{n1}\right) + 5.00 \; [DEG] \quad \text{Second Formula A}$$

$$\frac{\lambda}{2 \cdot \pi \cdot n1 \cdot \sqrt{\sin^2\theta - \left(\frac{n2}{n1}\right)^2}} \geqq 4 \; [\mu m] \quad \text{Third Formula A}$$

In the present embodiment, when it is assumed that the refractive index n2 of the object to be measured S with respect to the light including wavelengths of 10 µm is 1.44 and the light having the wavelength of 10 µm is incident on the total reflection plane at the incident angle θ, it is desired that the refractive index n1 satisfy the fourth formula and fifth formula given below.

$$\theta = \arcsin\left(\frac{n2}{n1}\right) + 0.8 \; [DEG] \quad \text{Fourth Formula}$$

$$\frac{\lambda}{2 \cdot \pi \cdot n1 \cdot \sqrt{\sin^2\theta - \left(\frac{n2}{n1}\right)^2}} \geqq 10 \; [\mu m] \quad \text{Fifth Equation}$$

In the present embodiment, it is desired that the refractive index n1 of the base material of the total internal reflection (TIR) prism be greater than 1.32 and be equal to or smaller than 1.91, and it is even more desirable that the refractive index n1 of the base material of the total internal reflection prism be greater than 1.32 and be equal to or smaller than 1.57. By setting the refractive index n1 as described above, the degree of penetration depth dp into the object to be measured S can be increased, and the ranges of angle for the degree of penetration depth dp can be widened. From the viewpoint of increasing the level of glucose absorbance and increasing the level of sensitivity in the measurement of blood sugar level, it is desired that the wavelength of the light be equal to or wider than 7 micrometers (µm) and equal to or narrower than 12 µm.

Figure 4:
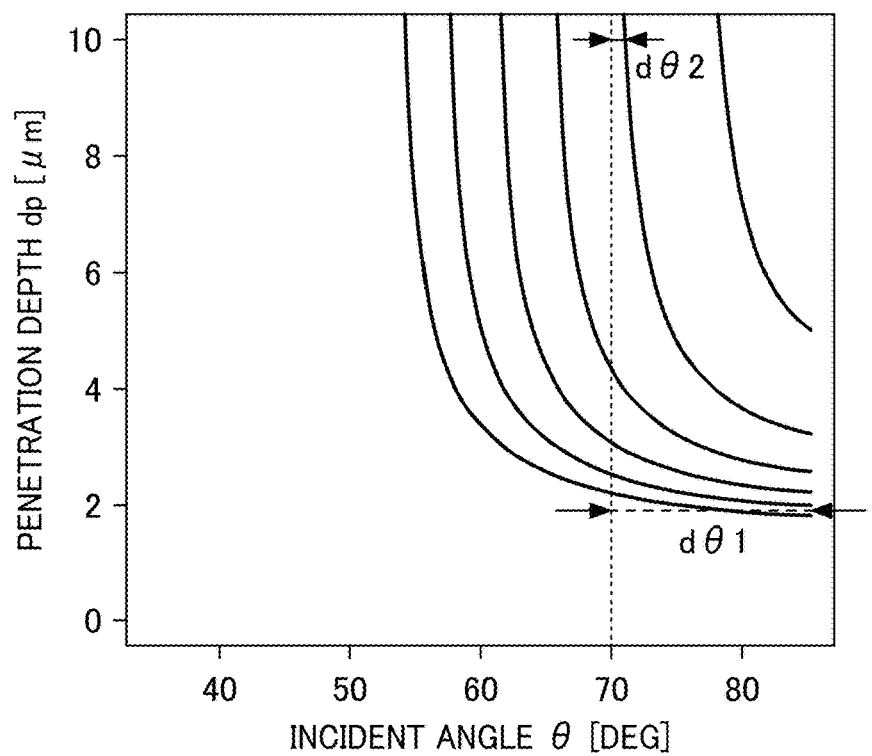
FIG. 4 is the third diagram illustrating the relation between the penetration depth and the incident angle, according to the related art.

FIG. 4 is a diagram illustrating the relation between the penetration depth and the incident angle θ, according to the third example of the present disclosure.

FIG. 4 illustrates the penetration depth dp when the refractive index of an object to be measured is changed and the refractive index n1 of the base material of a total internal reflection (TIR) prism is made equivalent to 1.49 that is the refractive index of sodium chloride (NaCl). The multiple graphs in FIG. 4 illustrate the relations between the penetration depth dp and the incident angles θ in the order from the smallest value to the largest value of the incident angle θ in the multiple cases where the refractive indexes n2 are 1.20, 1.25, 1.30, 1.35, 1.40, and 1.45, respectively.

As illustrated in FIG. 4, regardless of the value the refractive index n2 takes, the penetration depth dp increases as the incident angle θ gets close to the critical angle θ0. If the base material that includes sodium chloride (NaCl) is used, the ranges of both incident angle dθ1 and dθ2 became deeper compared with cases as illustrated in FIG. 1 in which a base material with a relatively high refractive index such as germanium (Ge) and zinc sulfide (ZnS) is used. The range of incident angle dθ1 indicates the range of the incident angle θ where the penetration depth dp becomes equal to or greater than 2 µm when the refractive index n2 is 1.40. The range of incident angle dθ2 indicates the range of the incident angle θ where the penetration depth dp becomes equal to or greater than 10 µm when the refractive index n2 is 1.40. When the ranges of incident angles dθ1 and dθ2 become deeper, the allowable range of the incident angle θ with which the penetration depth dp can have a desired depth is sufficiently wide.

As a light source in a mid-infrared range of about 9 µm to 10 µm, a multiple-wavelength light source having a continuous spectrum is used in many cases. Typically, a multiple-wavelength light source emits a plurality of diffusive light rays that are not parallel to each other. When the allowable range of the incident angle θ to the total reflection plane is relatively wide, the radiation intensity of the light that penetrates into the object to be measured can be increased even with a multiple-wavelength light source that emits a plurality of diffusive light rays that are not parallel to each other.

For example, when the allowable range of the incident angle θ that the light forms with the total reflection plane is narrow, an optical element such as an aperture or a lens used to adjust the incident angle θ to a desired angle needs to be arranged. As the allowable range of the incident angle θ is sufficiently wide, the light can be mitted to make the light incident on the total reflection plane easily at an incident angle within the allowable range without using any optical element. In cases where the incident angle of the light is adjusted using the optical elements, the loss in the radiation intensity of light tend to increase due to a slight misalignment if the allowable range of the incident angle θ is narrow. If the allowable range of the incident angle θ is sufficiently wide, even in cases where the incident angle of the light is adjusted using the optical elements, measurement can be performed using the ATR with reduced loss in the radiation intensity of light.

As described above, even with low-power evanescent-wave light, the allowable range of the incident angle θ may be widened to facilitate and achieve a sufficient radiation intensity of light. As a result, the signal-to-noise (S/N) ratio of measurement increases, and a measurement device with a high degree of reliability can be provided. With increased radiation intensity of light, a simple and inexpensive photodetector may be adopted, and it is advantageous in, for example, cost reduction and reduction in size and weight for the measurement device.

A measuring device according to embodiments of the present disclosure is described below in detail.

First Embodiment

Figure 5:
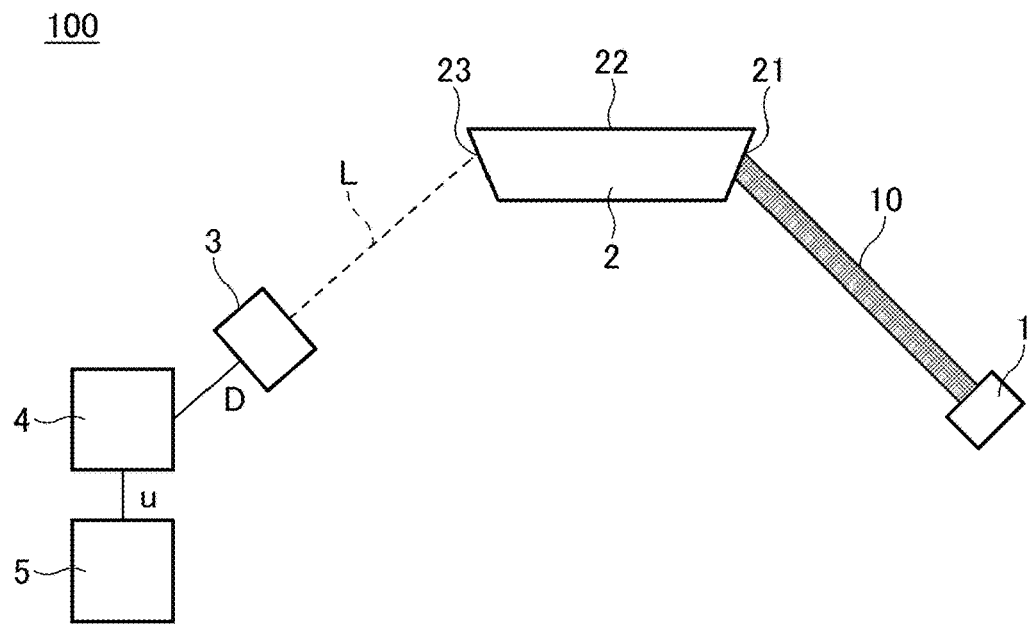
FIG. 5 is a diagram illustrating a configuration or structure of a measuring device according to a first embodiment of the present disclosure.

FIG. 5 is a diagram illustrating a configuration or structure of the measuring device 100 according to the first embodiment of the present disclosure.

Figure 6:
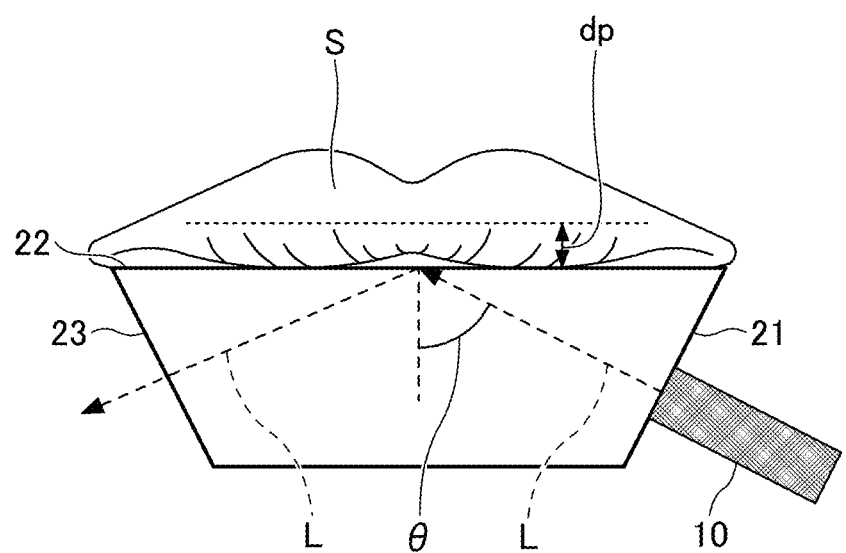
FIG. 6 is a diagram illustrating how a total internal reflection (TIR) prism contacts a lip, according to the first embodiment of the present disclosure.

FIG. 6 is a diagram illustrating how the total internal reflection (TIR) prism 2 contacts a lip, according to the first embodiment of the present disclosure, where the lip is the object to be measured S.

The measuring device 100 according to the present embodiment serves as a blood-sugar level measuring device.

As illustrated in FIG. 5, the measuring device 100 according to the present embodiment is provided with a multiple-wavelength light source 1, the total internal reflection (TIR) prism 2 a sensor 3, a processor 4, and a display 5. The measuring device 100 guides the light L emitted from the multiple-wavelength light source 1 to the total internal reflection prism 2 by an optical fiber 10. The multiple-wavelength light source 1 according to the present embodiment serves as a light source that emits light including a wavelength equal to or greater than 7 micrometers (μm) and equal to or less than 12 μm to make the light incident on the total reflection plane 22 at the incident angle θc of the center of the light flux. The measuring device 100 may include a light guide other than the optical fiber 10.

The total internal reflection (TIR) prism 2 according to the present embodiment includes an optical entrance 21, a total reflection plane 22 that contacts the object to be measured S, and an optical exit 23. The light L incident on the optical entrance 21 enters the total reflection plane 22. While the light is being totally reflected by the total reflection plane 22, an evanescent wave is generated outside the total reflection plane 22. In other words, an evanescent wave is generated toward the object to be measured S while the light is being totally reflected by the total reflection plane 22.

The evanescent wave penetrates into the object to be measured S that contacts the total reflection plane 22, and undergoes light attenuation according to the absorbance spectrum of the object to be measured. The light L that has undergone the light attenuation for the evanescent wave while being totally reflected by the total reflection plane 22 passes through the optical exit 23, and is emitted to the outside of the total internal reflection prism 2. Then, the light L is received by the sensor 3. An optical fiber that guides the light L may be further arranged between the total internal reflection prism 2 and the sensor 3.

The sensor 3 detects the light intensity D of the light L reflected by the total reflection plane 22. Then, the sensor 3 outputs the electrical signal according to the detected light intensity D to the processor 4. The processor 4 according to the present embodiment computes and obtains the absorbance data related to the absorbance in the object to be measured S, based on the light intensity D detected by the sensor 3. Moreover, the processor 4 computes and obtains the blood-sugar level data u related to the blood sugar level based on the absorbance data, and outputs the blood-sugar level data u to the display 5.

The display 5 according to the present embodiment displays the blood-sugar level data u output from the processor 4. The processor 4 according to the present embodiment can also output the blood-sugar level data u to a storage unit of blood-sugar level data u or a transmission unit of the blood-sugar level data u in addition to the display 5.

The total internal reflection (TIR) prism 2 according to the present embodiment includes sodium chloride (NaCl). As illustrated in FIG. 6, the light L incident on the optical entrance 21 is once totally reflected by the total reflection plane 22. In the present specific embodiment, the incident angle θc of the center of the light flux of the light L to the total reflection plane 22 is 63.0 degrees that is slightly wider than the critical angle θ0, i.e., 62.8 degrees. It is desired that the incident angle θc at the center of the emitted light flux be within a range between the critical angle θ0 and "θ0+5.0 degrees." However, in a case where a sufficient radiation intensity of light can be obtained even in a region deviating from the center of the light flux, measurement can be done even if the incident angle θc is out of the range between the critical angle θ0 and "θ0+5.0 degrees." For example, the measuring device 100 can perform measurement when the inner surface of the upper lip that serves as the object to be measured S contacts the total reflection plane 22.

Figure 7:
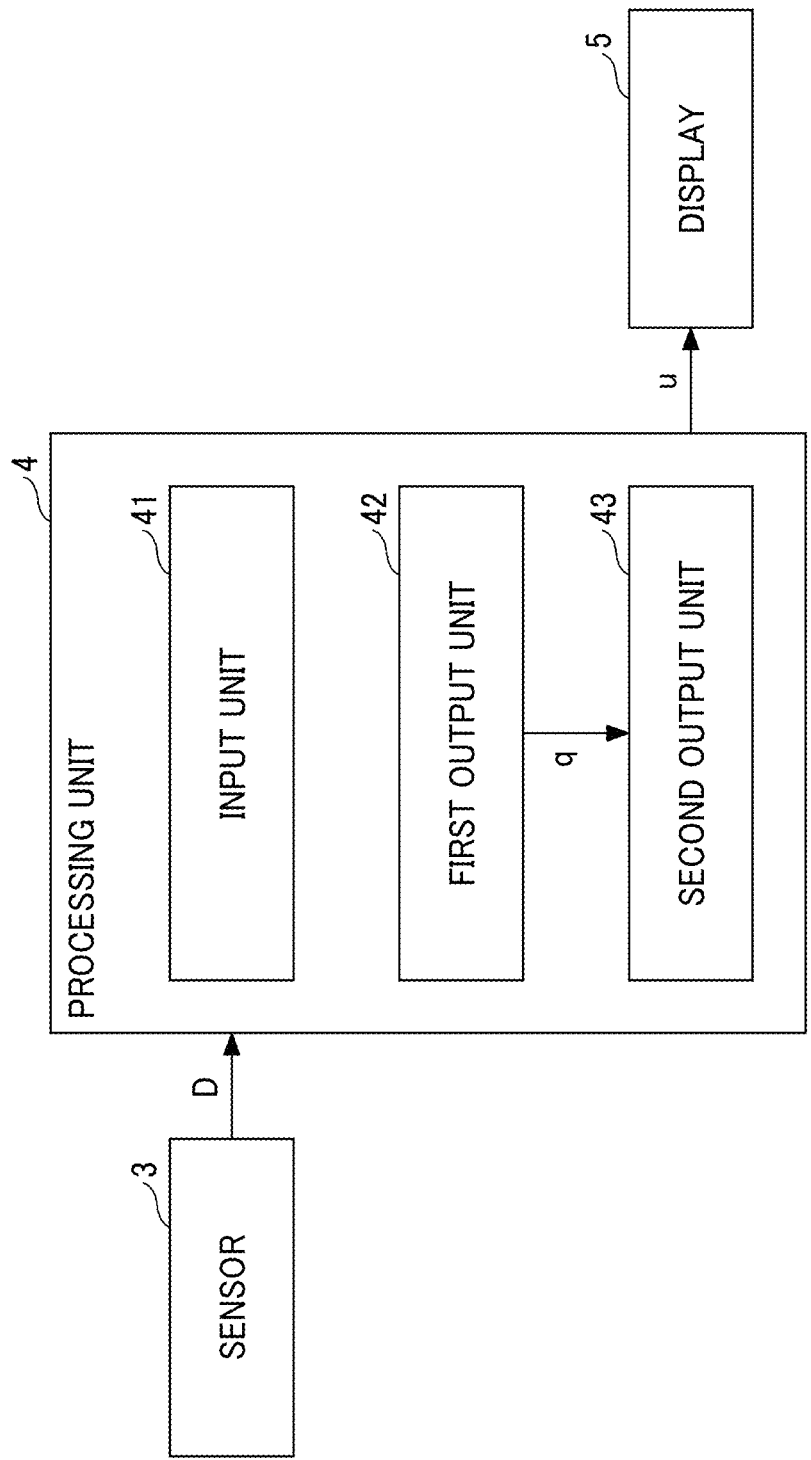
FIG. 7 is a block diagram of a functional configuration of a processor according to the first embodiment of the present disclosure.

FIG. 7 is a block diagram illustrating a functional configuration of the processor 4, according to the first embodiment of the present disclosure.

The processor 4 according to the present embodiment includes an input unit 41, a first output unit 42, and a second output unit 43. The processor 4 implements these multiple functions by an electric circuit. Alternatively, the processor 4 may implement at least some of these functions by software using a central processing unit (CPU). Alternatively, these functions of the processor 4 may be implemented by a plurality of electric circuits or a plurality of software components.

The first output unit 42 receives an electrical signal according to the light intensity D detected by the sensor 3 through the input unit 41, and outputs the absorbance data q based on the light intensity D. For example, the sensor 3 according to the present embodiment outputs the light intensity D to the processor 4 for each wavelength, and the first output unit 42 can output the absorbance data q obtained by computation based on the light intensity D for each wavelength.

The second output unit 43 outputs the blood-sugar level data u based on the absorbance data q sent from the first output unit 42. For example, the second output unit 43 analyzes the absorbance data q to obtain blood-sugar level data u, and can output the blood-sugar level data u to the display 5.

The second output unit 43 can also output the live-subject information in addition to the blood-sugar level data u. For example, the live-subject information includes the information about composition included in a live subject, and the information about composition includes the information about at least one of glucose, skin tissue, collagen, and lipid.

Figure 8:
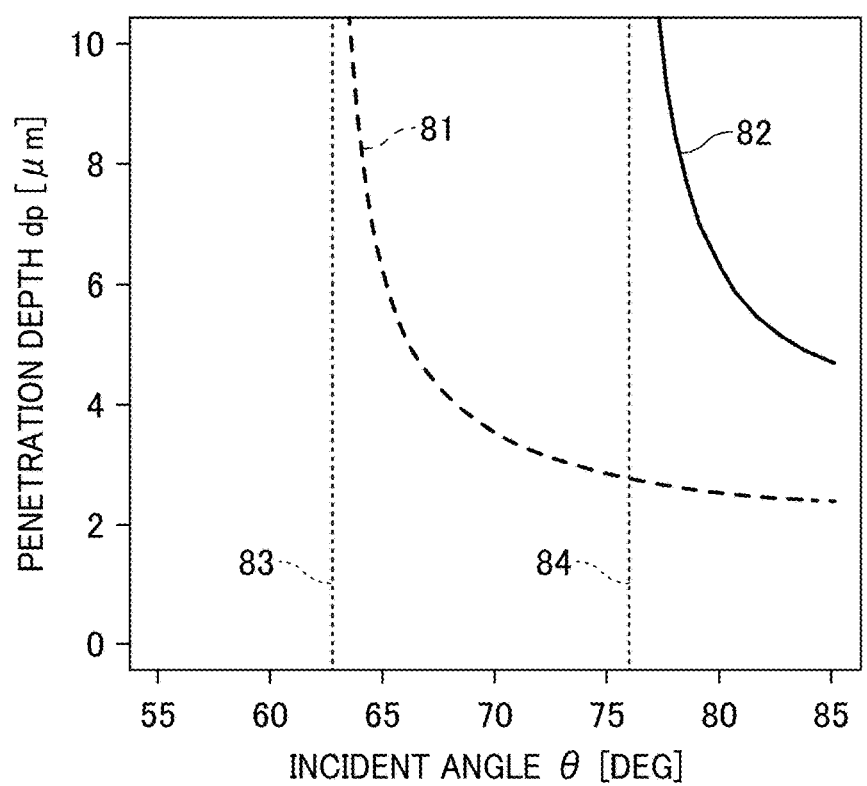
FIG. 8 is the first diagram illustrating the relation between the penetration depth and the incident angle, according to the first embodiment of the present disclosure.
Figure 9:
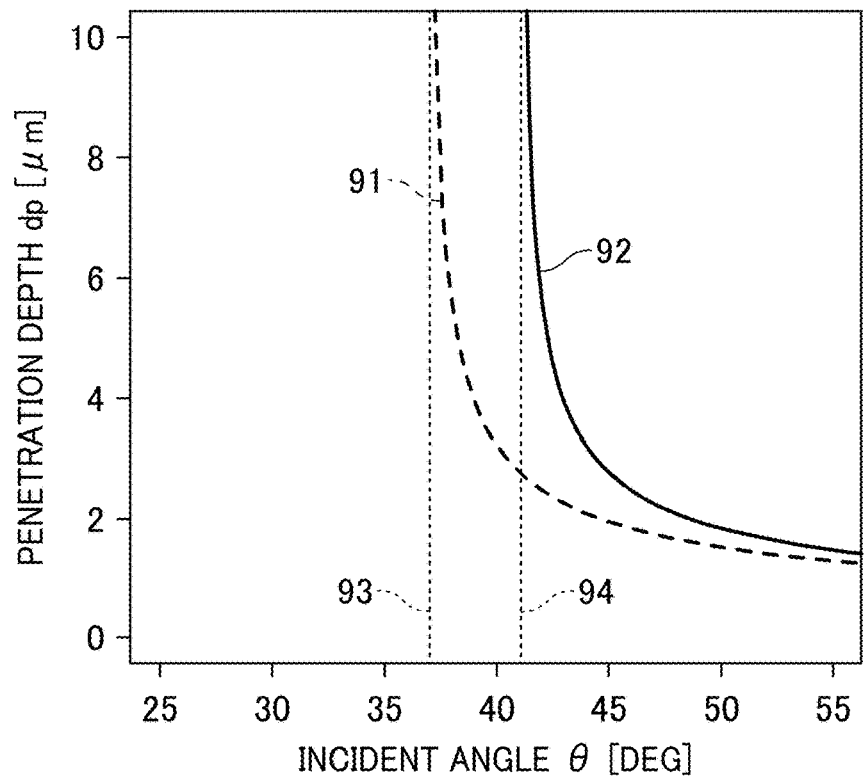
FIG. 9 is the second diagram illustrating the relation between the penetration depth and the incident angle, according to the first embodiment of the present disclosure.
Figure 10:
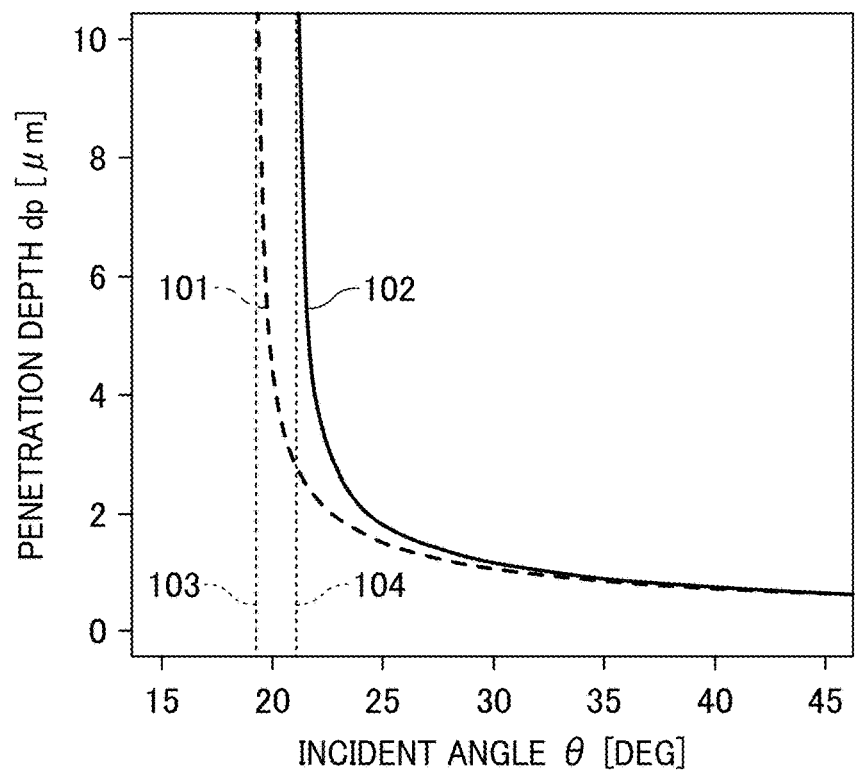
FIG. 10 is the third diagram illustrating the relation between the penetration depth and the incident angle, according to the first embodiment of the present disclosure.

FIG. 8, FIG. 9, and FIG. 10 are diagrams each illustrating the relation between the penetration depth dp and the incident angle θ, according to the first embodiment of the present disclosure.

FIG. 8 is the first diagram illustrating the relation between the penetration depth dp and the incident angle θ, according to the first embodiment of the present disclosure.

FIG. 9 is the second diagram illustrating the relation between the penetration depth dp and the incident angle θ, according to the first embodiment of the present disclosure.

FIG. 10 is the third diagram illustrating the relation between the penetration depth dp and the incident angle θ, according to the first embodiment of the present disclosure.

FIG. 8 illustrates the relation between the penetration depth dp and the incident angle θ when the refractive index n1 is 1.490 and the refractive index n2 is 1.32 and 1.44, according to the first embodiment of the present disclosure.

The refractive index n1 in FIG. 8 is the refractive index of the base material of the total internal reflection (TIR) prism 2 that includes sodium chloride (NaCl). The graph 81 that is indicated by dashed lines indicates the case of a lip whose refractive index n2 is about 1.32, and the graph 82 that is indicated by a solid line indicates the case of a finger whose refractive index n2 is about 1.44. The graph 83 according to the present embodiment indicates 62.8 degrees that is equivalent to the critical angle θ0 when the refractive index n2 is 1.32. The graph 84 according to the present embodiment indicates 75.9 degrees that is equivalent to the critical angle θ0 when the refractive index n2 is 1.44.

The penetration depth dp decreases sharply in response to the deviation from the critical angle θ0. For this reason, it is desired that the light L be emitted at the incident angle θc within a range of deviation of 5.0 degrees from the critical angle θ0. For this reason, the incident angle θc is arranged to have 63.0 degrees in the first embodiment of the present disclosure.

FIG. 9 illustrates the relation between the penetration depth dp and the incident angle θ when the refractive index n1 is 2.20 and the refractive index n2 is 1.32 and 1.44, according to the first embodiment of the present disclosure.

The refractive index n1 in FIG. 9 is the refractive index of the base material of the total internal reflection prism 2 that includes zinc sulfide (ZnS).

The graph 91 that is indicated by dashed lines indicates the case of a lip whose refractive index n2 is about 1.32, and the graph 92 that is indicated by a solid line indicates the case of a finger whose refractive index n2 is about 1.44. The graph 93 according to the present embodiment indicates 37.0 degrees that is equivalent to the critical angle θ0 when the refractive index n2 is 1.32. The graph 94 according to the present embodiment indicates 41.1 degrees that is equivalent to the critical angle θ0 when the refractive index n2 is 1.44. For example, the incident angle θc of the center of the light flux emitted from the light source may be 37.0 degrees when a lip is to be measured, and the incident angle θc of the center of the light flux emitted from the light source may be 42.0 degrees when a finger is to be measured.

FIG. 10 illustrates the relation between the penetration depth dp and the incident angle θ when the refractive index n1 is 4.00 and the refractive index n2 is 1.32 and 1.44, according to the first embodiment of the present disclosure.

The refractive index n1 in FIG. 10 is the refractive index of the base material of the total internal reflection (TIR) prism 2 that includes germanium (Ge).

The graph 101 that is indicated by dashed lines indicates the case of a lip whose refractive index n2 is about 1.32, and the graph 102 that is indicated by a solid line indicates the case of a finger whose refractive index n2 is about 1.44. The graph 103 according to the present embodiment indicates 19.3 degrees that is equivalent to the critical angle θ0 when the refractive index n2 is 1.32. The graph 104 according to the present embodiment indicates 21.2 degrees that is equivalent to the critical angle θ0 when the refractive index n2 is 1.44. The incident angle θc of the center of the light flux emitted from the light source can be changed to 20.0 degrees when a lip is to be measured, and can be changed to, for example, 22.0 degrees when a finger is to be measured.

Figure 11:
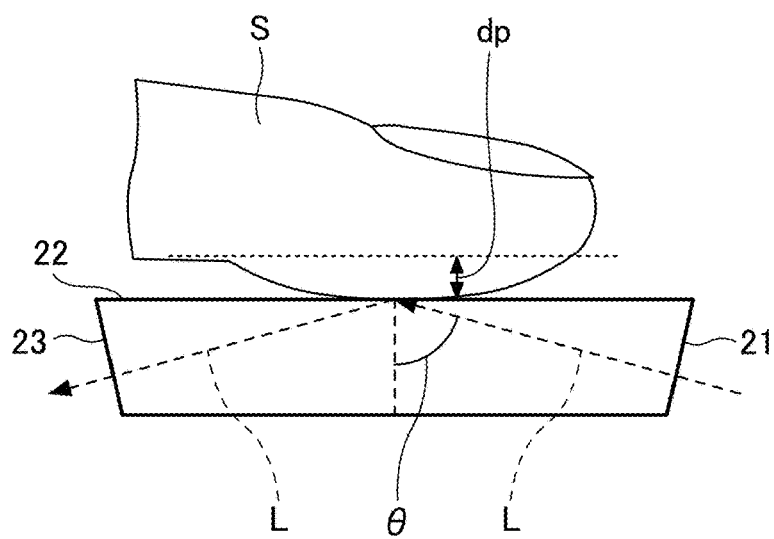
FIG. 11 is a diagram illustrating a case in which an object to be measured is a finger, according to the first embodiment of the present disclosure.

FIG. 11 is a diagram illustrating a case in which the object to be measured S is a finger, according to the first embodiment of the present disclosure.

As illustrated in FIG. 11, the light L incident on the optical entrance 21 is once totally reflected by the total reflection plane 22. In the present embodiment, the incident angle θc of the center of the light flux of the light L to the total reflection plane 22 is 76.0 degrees which is slightly smaller than the critical angle θ0. For example, the measuring device 100 can perform measurement when the belly of the finger that serves as the object to be measured S contacts the total reflection plane 22.

In the attenuated total reflection (ATR), for example, there are some cases in which a sufficient degree of sensitivity in the measurement cannot be obtained as the amount of component that absorbs light is small in the object to be measured S. In order to avoid such a situation, the light may be totally reflected a plurality of times by the total internal reflection prism 2 to increase the sensitivity in the measurement.

Figure 12:
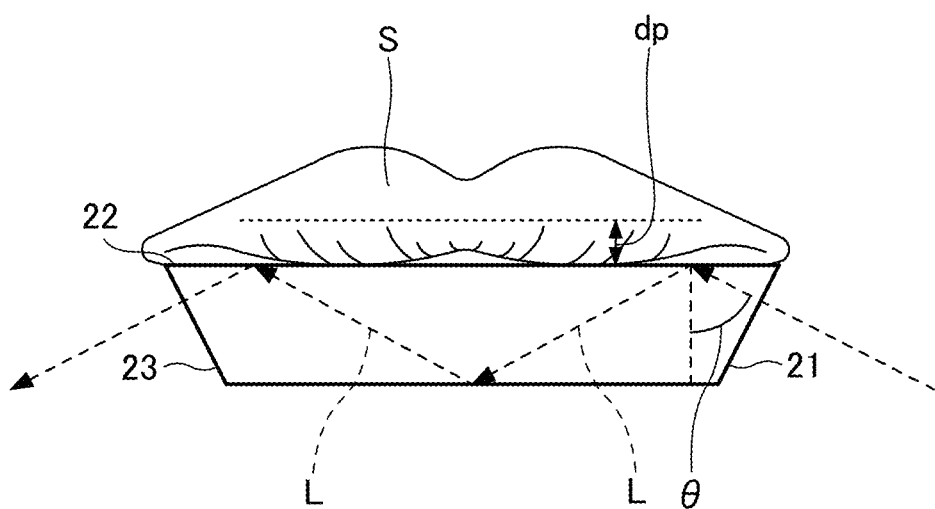
FIG. 12 is a diagram illustrating a configuration or structure in which the light is totally reflected a plurality of times by a total internal reflection prism, according to the first embodiment of the present disclosure.

FIG. 12 is a diagram illustrating a configuration or structure in which the light is totally reflected a plurality of times by the total internal reflection prism 2, according to the first embodiment of the present disclosure.

For example, the thickness of the total internal reflection prism 2 may be made thin to increase the number of times the light is reflected. In the present embodiment described with reference to FIG. 12, the light is totally reflected twice by the total reflection plane 22. As the number of times the light is totally reflected increases, the amount of absorbance light increases. For this reason, in the present embodiment described with reference to FIG. 12, the degree of reliability in the above measurement can be increased compared with the cases in which the light is totally reflected one time.

Second Embodiment

A measuring device 100a according to the second embodiment of the present disclosure is described below. In view of the first embodiment of the present disclosure as described above, like reference signs denote like elements, and redundant description may be omitted where appropriate.

A configuration or structure of the measuring device 100a according to the second embodiment of the present disclosure is described below with reference to FIG. 13A, FIG. 13B, FIG. 14, and FIG. 15.

Figure 13A:
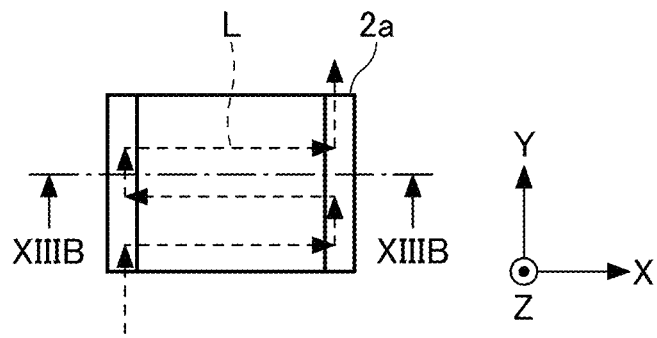
FIG. 13A and FIG. 13B are diagrams each illustrating a configuration or structure of a measuring device according to a second embodiment of the present disclosure.
Figure 13B:
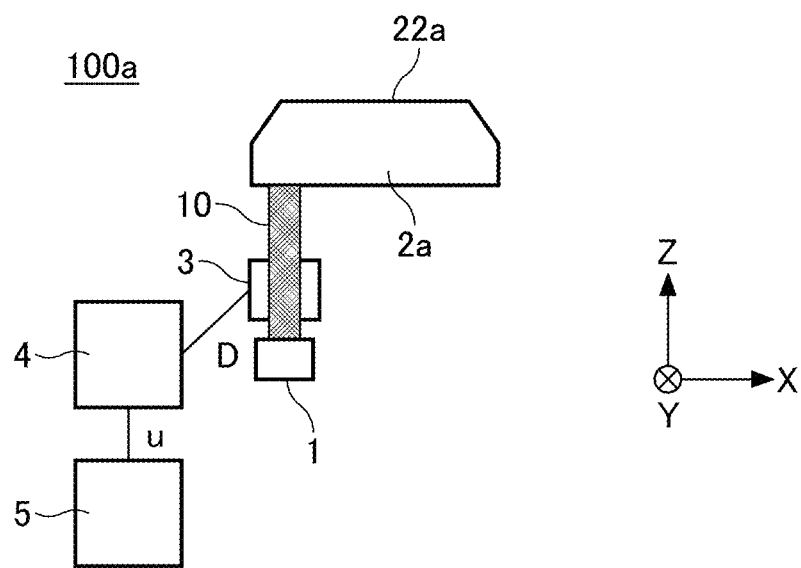

FIG. 13A and FIG. 13B are diagrams each illustrating a configuration or structure of the measuring device 100a according to the second embodiment of the present disclosure.

More specifically, FIG. 13A is a top view of the measuring device 100a according to the second embodiment of the present disclosure, and FIG. 13B is a XIIIB-XIIIB sectional view of the measuring device 100a as illustrated in FIG. 13A.

Figure 14:
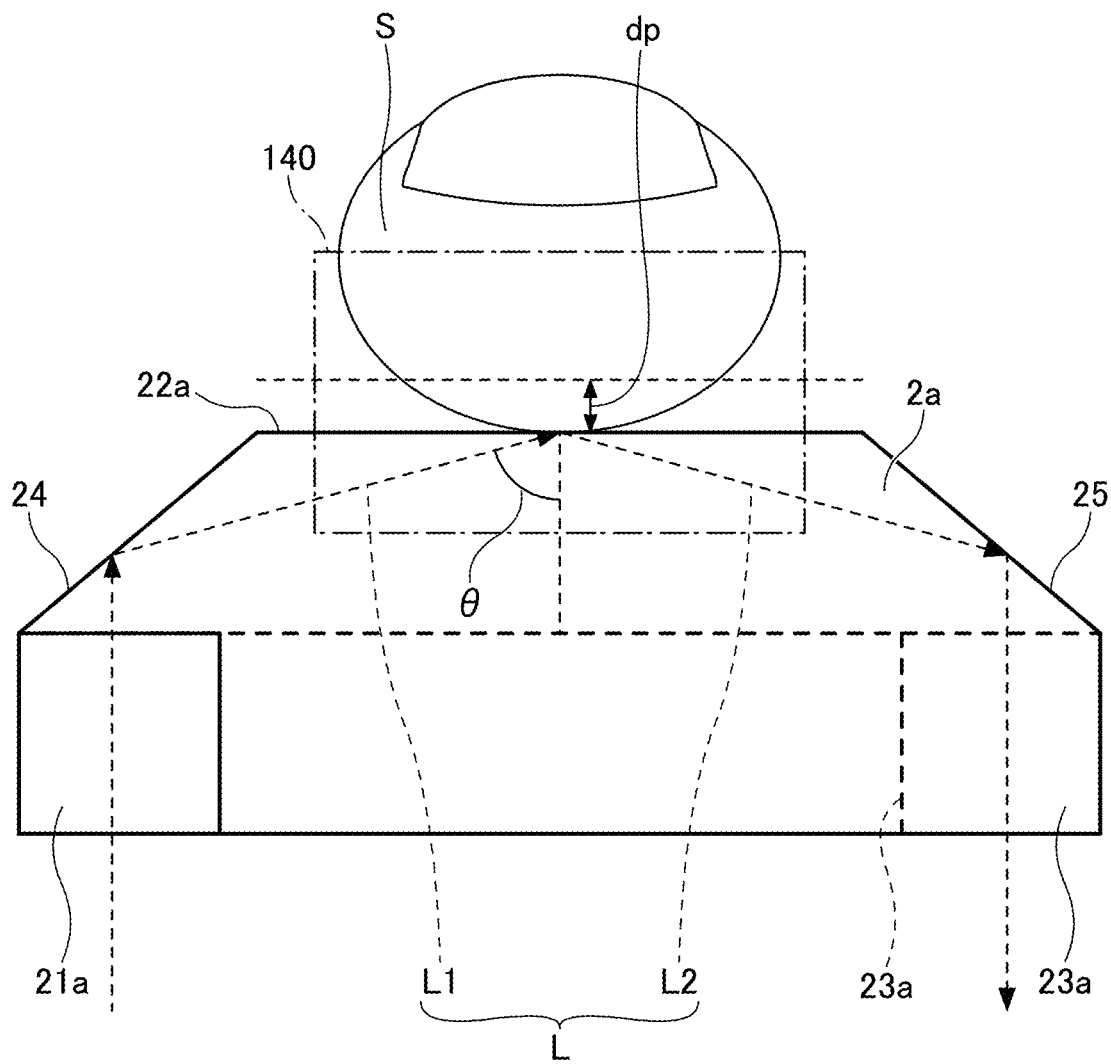
FIG. 14 is a front view of a total internal reflection prism provided for a measuring device according to the second embodiment of the present disclosure.
Figure 15:
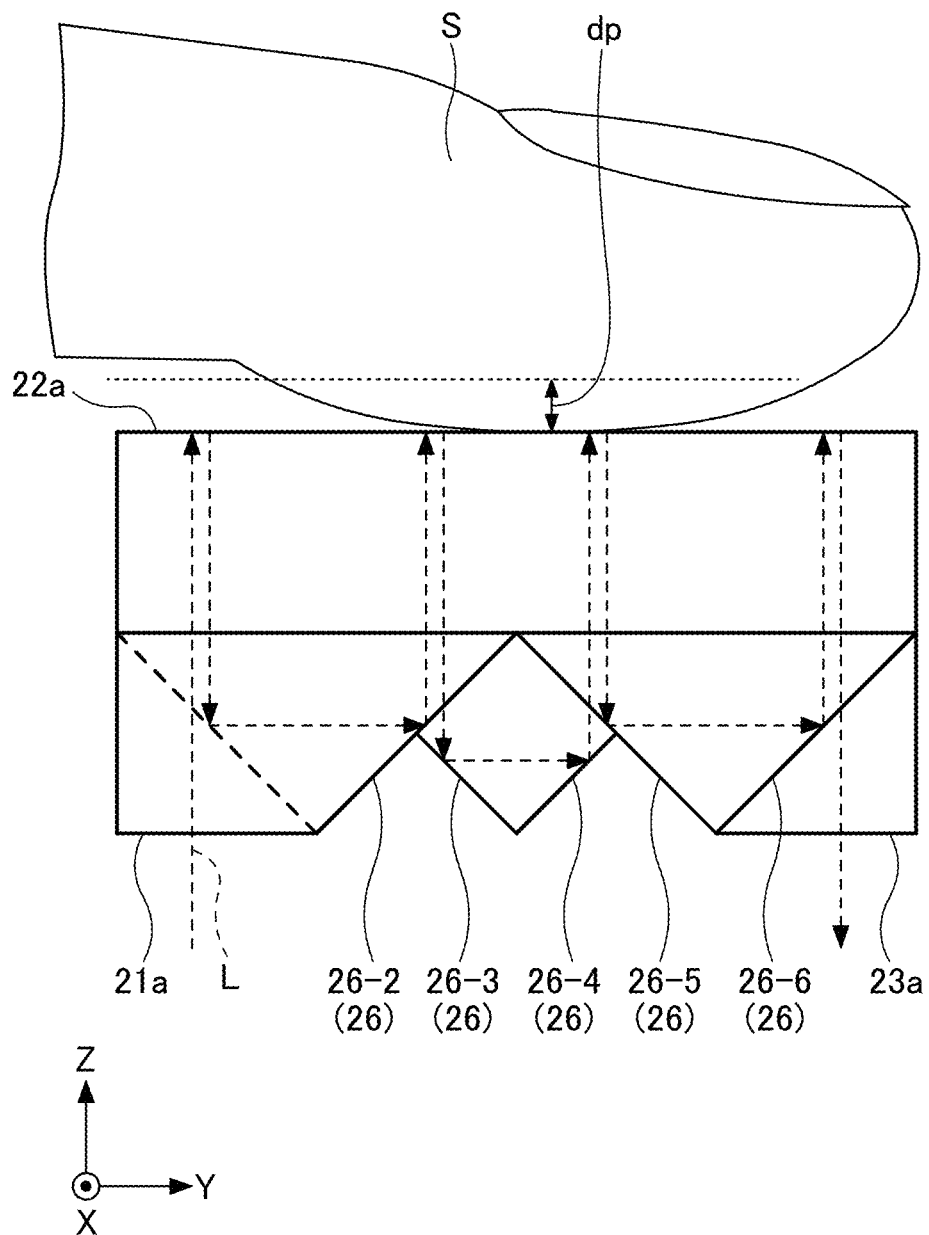
FIG. 15 is a side view of a total internal reflection prism provided for a measuring device according to the second embodiment of the present disclosure.

FIG. 14 and FIG. 15 are diagrams each illustrating a total internal reflection prism 2a provided for the measuring device 100a according to the second embodiment of the present disclosure.

FIG. 14 is a front view of the total internal reflection prism 2a provided for the measuring device 100a according to the second embodiment of the present disclosure.

FIG. 15 is a side view of the total internal reflection prism 2a provided for the measuring device 100a according to the second embodiment of the present disclosure.

As illustrated in FIG. 13A, FIG. 13B, FIG. 14, and FIG. 15, the total internal reflection prism 2a is provided for the measuring device 100a according to the second embodiment of the present disclosure.

The total internal reflection (TIR) prism 2a according to the second embodiment of the present disclosure is provided with a plurality of cross-reflective planes 26 that reflect the light L in a direction intersecting with an incident plane 140 that includes thereon an incident light beam L1 and a reflected light beam L2 of the light L on a total reflection plane 22a.

The multiple cross-reflective planes 26 provided for the total internal reflection prism 2a according to the present embodiment include a cross-reflective plane 26-1, a cross-reflective plane 26-2, a cross-reflective plane 26-3, a cross-reflective plane 26-4, a cross-reflective plane 26-5, and a cross-reflective plane 26-6.

As illustrated in FIG. 14 and FIG. 15, the light L incident on the optical entrance 21a is reflected by the first reflection plane 24, the total reflection plane 22a, and the second reflection plane 25 in the order listed, and then the light is reflected by the cross-reflective plane 26-1 in a direction intersecting the incident plane 140. In the present embodiment, the direction that intersects with the incident plane 140 is parallel to the Y-axis forward direction that is the direction in which the arrow indicating the Y-axis points.

The light L that is reflected by the cross-reflective plane 26-1 is reflected by the cross-reflective plane 26-2, the first reflection plane 24, the total reflection plane 22$a$, the second reflection plane 25, the cross-reflective plane 26-3, the cross-reflective plane 26-4, the first reflection plane 24, the total reflection plane 22$a$, the second reflection plane 25, the cross-reflective plane 26-5, the cross-reflective plane 26-6, the first reflection plane 24, the total reflection plane 22$a$, the second reflection plane 25, in the order listed. After that, the light is emitted from the optical exit 23$a$. In the present embodiment, the light L is totally reflected four times by the total reflection plane 22$a$.

In the second embodiment of the present disclosure, the light L incident on the optical entrance 21$a$ is reflected and emitted in a direction parallel to the incident direction and in the reverse direction to the incident direction. In view of such a configuration and structure, it can be said that the total internal reflection prism 2$a$ comprises a retroreflector or retroreflection mechanism.

When sodium chloride (NaCl) is used as the base material of the total internal reflection prism, the incident angle θ with which the light L is totally reflected by the total reflection plane increases compared with the cases in which germanium (Ge) or the like is used. In view of these circumstances, the number of times the light is to be totally reflected, which tends to be increased in order to increase the sensitivity in the measurement, is limited compared with the cases in which germanium (Ge) or the like is used.

With the total internal reflection prism 2$a$ provided for the measuring device 100$a$ according to the second embodiment of the present disclosure, the number of times the light is totally reflected by the total reflection plane 22$a$ may be increased to increase the level of sensitivity in the measurement by the measuring device 100$a$ even when the incident angle θc of the center of the light flux emitted from the light source is increased.

Cases in which the object to be measured S is a finger are described with reference to FIG. 14 and FIG. 15. However, no limitation is indicated thereby, and similar advantageous effects can be achieved when the object to be measured S is a lip. In FIG. 14 and FIG. 15, the multiple cross-reflective planes 26 according to the second embodiment of the present disclosure are inclined at 45 degrees with respect to the light L incident on the total internal reflection prism 2$a$. However, no limitation is indicated thereby. The tilt angle that the multiple cross-reflective planes 26 form with the light L incident on the total internal reflection prism 2$a$ is satisfactory as long as the incident angle of the light is smaller than about 42 degrees that is the critical angle of the total internal reflection prism 2$a$ that includes sodium chloride (NaCl) as part of its base material for the air whose refractive index is 1.0.

Other Alternative Embodiments

When the base material of the total internal reflection (TIR) prism includes sodium chloride (NaCl), the total-reflection prism may deliquesce. Deliquescence is a phenomenon in which a substance absorbs water in the air and becomes an aqueous solution. The total internal reflection prism that includes sodium chloride (NaCl) as part of its base material may be deformed or altered due to deliquescence. For this reason, it has been difficult in the related art to use the total internal reflection prism including sodium chloride (NaCl) as part of its base material under normal temperature and humidity environments. Under such normal temperature and humidity environments, typically, the temperature is equal to or higher than 17 degrees on the Celsius scale and equal to or lower than 28 degrees, and the relative humidity is equal to or higher than 40% and equal to or lower than 70%.

In the present embodiment, in order to prevent deformation or alteration due to deliquescence, a coating layer may be arranged to coat or cover the surface of the total internal reflection prism that includes sodium chloride (NaCl) as part of its base material. For example, a coating film that has a thickness of about 550 nanometers (nm) and includes aluminum oxide ($Al_2O_3$) may be formed on the surface of the total reflecting prism using an atomic layer deposition film formation technique. By so doing, the coating film can be formed.

The atomic layer deposition technique is a technique for forming a thin film using a chemical reaction in a continuous gas phase. Due to the atomic layer deposition technique, the film thickness and the material can be controlled at an atomic layer level, and a very thin and dense film can be formed. A film of aluminum oxide ($Al_2O_3$) can be formed at a relatively low temperature. As sodium chloride (NaCl) is a brittle material with low thermal resistance, a film formation method using an atomic layer deposition film forming technique is suitable.

A measuring device according to embodiments of the present disclosure may use a total internal reflection prism with a coating layer on its surface. Due to such a configuration, the total internal reflection (TIR) prism that includes sodium chloride (NaCl) as part of its base material can be used under normal temperature and humidity environments. The total internal reflection prism provided with the coating film can prevent the deliquescence caused by cleaning process. Accordingly, the total reflecting prism can be repeatedly used while cleaning the total reflecting prism after the measurement. As it is not always necessary to dispose of the total reflecting prism for each measurement, it is competitive costwise. Further, as it is not always necessary to detach and attach the total-reflection prism for each measurement, the measurement can be performed efficiently.

Numerous additional modifications and variations are possible in light of the above teachings. It is therefore to be understood that within the scope of the appended claims, the disclosure of the present disclosure may be practiced otherwise than as specifically described herein. For example, elements and/or features of different illustrative embodiments may be combined with each other and/or substituted for each other within the scope of this disclosure and appended claims.

Embodiments of the present disclosure also includes a measuring method as follows. For example, in such a measuring method, light is emitted by a light source, and the light including a wavelength of 10 μm is made incident on a total reflection plane that an object to be measured contacts, at an incident angle θc. Moreover, in such a measuring method, the light intensity of the light reflected by the total reflection plane is detected by a sensor, and absorbance data related to absorbance in the object to be measured is output by a first output unit, based on the light intensity detected by a sensor. Moreover, in such a measuring method, live-subject information that is information about a live subject is output by a second output unit, based on the absorbance data, and the incident angle θc is expressed by the first formula given above, where n1 denotes a refractive index of a base material of a total internal reflection prism for the light, and n2 denotes a refractive index of the object to be measured and n2 has a value 1.32 or 1.44. With such a measuring method, functions similar to those implemented by the measuring device 100 can be implemented.

Each of the functions of the described embodiments may be implemented by one or more processing circuits or circuitry. Processing circuitry includes a programmed processor, as a processor includes circuitry. The one or more processing circuits herein includes, for example, devices such as a processor that is programmed to execute software to implement functions, like a processor with electronic circuits, an application-specific integrated circuit (ASIC) that is designed to execute the above functions, a digital signal processor (DSP), a field-programmable gate array (FPGA), and a circuit module or circuit components known in the art arranged to perform the recited functions.

Any one of the above-described operations may be performed in various other ways, for example, in an order different from the one described above.

What is claimed is:

1. A measuring device comprising:
   a total internal reflection prism having a total reflection plane that an object to be measured contacts;
   a light source configured to emit light to make the light having a wavelength equal to or greater than 7 micrometers (μm) and equal to or less than 12 μm incident on the total reflection plane; and
   a sensor configured to detect light intensity of the light reflected by the total reflection plane,
   wherein an equation $$\arcsin\left(\frac{n2}{n1}\right) < \theta c < \arcsin\left(\frac{n2}{n1}\right) + 5.0 \ [DEG]$$

is satisfied, where
   n1 denotes a refractive index of a base material of the total internal reflection prism for the light having a wavelength of 10 μm,
   n2 denotes a refractive index of the object to be measured for the light having the wavelength of 10 μm and n2 takes a value 1.32 or 1.44, and
   θc denotes an incident angle of a center of light flux emitted from the light source.

2. The measuring device according to claim 1,
   wherein the refractive index n1 of the base material is equal to or greater than 1.32 and equal to or smaller than 1.91, and
   wherein an equation $$43.9 < \theta c < 90.0 [DEG]$$

is satisfied.

3. The measuring device according to claim 1,
   wherein the refractive index n1 of the base material is equal to or greater than 1.32 and equal to or smaller than 1.57
   wherein an equation $$67.0 < \theta c < 90.0 [DEG]$$

is satisfied.

4. The measuring device according to claim 1,
   wherein the base material includes sodium chloride.

5. The measuring device according to claim 1,
   wherein the base material includes a coating film that covers a surface of the base material.

6. The measuring device according to claim 5,
   wherein the coating film includes aluminum oxide.

7. The measuring device according to claim 1,
   wherein the total internal reflection prism is configured to make the light totally reflected a plurality of times inside the total internal reflection prism.

8. The measuring device according to claim 1,
   wherein the total internal reflection prism includes a cross-reflective plane to reflect the light in a direction intersecting with an incident plane including an incident light beam and a reflected light beam of the light on the total reflection plane.

9. The measuring device according to claim 1,
   wherein the object to be measured is a live subject.

10. The measuring device according to claim 1, further comprising:
    a first output device configured to output absorbance data related to absorbance in the object to be measured, based on the light intensity detected by the sensor; and
    a second output device configured to output live-subject information that is information about a live subject, based on the absorbance data output from the first output device.

11. The measuring device according to claim 10,
    wherein the live-subject information includes information about composition included in the live subject, and
    wherein the information about composition includes information about at least one of glucose, skin tissue, collagen, or lipid.

12. A measuring device comprising:
    a total internal reflection prism having a total reflection plane that an object to be measured contacts, the total internal reflection prism having a base material with a refractive index n1;
    a light source configured to emit light to make the light having a wavelength equal to or greater than 7 micrometers (μm) and equal to or less than 12 μm incident on the total reflection plane; and
    a sensor configured to detect light intensity of the light reflected by the total reflection plane,
    the refractive index n1 of the base material of the total internal reflection prism for the light having a wavelength of 10 μm being greater than 1.32 and equal to or smaller than 1.91.

13. The measuring device according to claim 12,
    wherein the refractive index n1 of the base material is greater than 1.32 and equal to or smaller than 1.57.

14. The measuring device according to claim 12,
    wherein the base material includes sodium chloride.

15. The measuring device according to claim 12,
    wherein the base material includes a coating film that covers a surface of the base material.

16. The measuring device according to claim 15,
    wherein the coating film includes aluminum oxide.

17. The measuring device according to claim 12,
    wherein the total internal reflection prism is configured to make the light totally reflected a plurality of times inside the total internal reflection prism.

18. The measuring device according to claim 12,
    wherein the total internal reflection prism includes a cross-reflective plane to reflect the light in a direction intersecting with an incident plane including an incident light beam and a reflected light beam of the light on the total reflection plane.

19. A blood-sugar level measuring device comprising the measuring device according to claim 10,
wherein the live-subject information includes information about a blood sugar level of blood included in the live subject.

20. A measuring method comprising:
emitting light to make the light including a wavelength equal to or greater than 7 μm and equal to or less than 12 μm incident on a total reflection plane that an object to be measured contacts;
detecting light intensity of the light reflected by the total reflection plane,
outputting absorbance data related to absorbance in the object to be measured, based on the light intensity detected by a sensor; and
outputting live-subject information that is information about a live subject, based on the absorbance data,
wherein an equation $$\arcsin\left(\frac{n2}{n1}\right) < \theta c < \arcsin\left(\frac{n2}{n1}\right) + 5.0 \ [DEG]$$

is satisfied, where
n1 denotes a refractive index of a base material of a total internal reflection prism for the light,
n2 denotes a refractive index of the object to be measured and n2 takes a value 1.32 or 1.44, and
θc denotes an incident angle of a center of light flux emitted from a light source.

* * * * *